United States Patent [19]
Alldread et al.

[11] Patent Number: 5,670,333
[45] Date of Patent: Sep. 23, 1997

[54] **EXPRESSION OF POLYPEPTIDES IN *E. COLI* UNDER CONTROL OF THE *E. COLI* MDH-GENE PROMOTER**

[75] Inventors: Richard M. Alldread; David J. Nicholls; Michael D. Scawen; Tony Atkinson, all of Salisbury, Great Britain

[73] Assignee: Public Health Laboratory Service Board, London, England

[21] Appl. No.: 211,682

[22] PCT Filed: Oct. 16, 1992

[86] PCT No.: PCT/GB92/01897

§ 371 Date: Jul. 28, 1994

§ 102(e) Date: Jul. 28, 1994

[87] PCT Pub. No.: WO93/08277

PCT Pub. Date: Apr. 29, 1993

[30] Foreign Application Priority Data

Oct. 16, 1991 [GB] United Kingdom ............... 9121965

[51] Int. Cl.$^6$ ............... C12P 21/00; C12N 15/64; C12N 15/67; C12N 15/70
[52] U.S. Cl. ............... 435/69.1; 435/172.3; 435/320.1; 536/23.1; 536/23.2; 536/23.5; 536/23.6; 536/23.7; 536/24.1
[58] Field of Search ............... 435/69.1, 172.3, 435/320.1; 536/23.1, 23.2, 23.5, 23.6, 23.7, 24.1

[56] References Cited

PUBLICATIONS

D.J. Nicholls et al, "Cloning sequencing and over-expression . . . ", Appl Microbiol Biotechnol (1989), 31, pp. 376–382.

R.F. Vogel et al, "Cloning and sequence of the mdh structural gene . . . " Arch. Microbiol (1987), 149, pp. 36–42.

David J. Nicholls et al, "Cloning and nucleotide sequences of the mdh and sucD–genes . . . ", FEMS Microbiology Letters, (1990), 70, pp. 7–14.

J.D. Hoheisel, "A cassette with seven unique restriction sites, . . . ", Gene (1989), 80, pp. 151–154.

D.M. Marquis, et al, "Use of a portable ribosome–binding site . . . " Gene (1986), 42, pp. 175–183.

Sambrook, J. et al, "Expression of cloned genes in *Escherichia coli*", Molecular Cloning, A laboratory manual, Second edition, pp. 17.2–17.44.

R.M. Alldread et al, "Overexpression of the *Thermus aquaticus* B malate . . . " Gene (1992), 114, pp. 139–143.

Yen (1991), J. Bact. 173 (17): 5328–5335.

*Primary Examiner*—Mindy Fleisher
*Assistant Examiner*—Nancy J. Degen
*Attorney, Agent, or Firm*—Nixon & Vanderhye

[57] ABSTRACT

Expression vector for expressing the *E. coli* a polypeptide other than *E. coli* malate dehydrogenase coded for by a DNA coding sequence. The vector includes a DNA coding for the polypeptide and also includes an initiation codon wherein the DNA sequence is operatively linked to an upstream sequence located upstream of the initiation codon and which is capable of controlling expression of the polypeptide. The upstream sequence consists on the 285 base pair sequence defined by SEQ ID NO:3. A process for expressing a polypeptide by culturing a host strain of *E. coli* transformed with an expression vector of the invention is also provided.

31 Claims, 5 Drawing Sheets

FIG. 2 pRMA4    GAAGGCCCTGGGCTAAAAAGGAGGTGGACG GTG AAG GCA CCC GTA ....
                            ‾‾‾‾‾‾‾‾‾‾‾‾‾  M   K   A   P   V  . .
                                S.D.

pRMA41   GAAGGCCCTGGGCTAAAAAGGAGGTGGCAT ATG AAG GCA CCC GTA ....
                            ‾‾‾‾‾‾‾‾‾‾‾‾‾  M   K   A   P   V  . .
                                S.D.

FIG. 4

```
SphI
GCATGCAAATTCTGCTTAAAAGTAAATTAATTGTTATCAAATTGATGTGTTTTGGCTGAACGGTAGGGTATATTGTCACCCTGTTGGAATGTTGCGC  100

TAATGCATAAGGCGACTGTTAATTACGTAAGTTAGGTTCCTGATTACGGCCAATTAAATGCATAAACTGCGTGACTACACATTCTTGAGATGTG  200
                                                      CRP
                                                                                       NdeI
GTCATTGTAAACGGCAATTTTGTGGATTAAGGTCGGGGCAGCGGGAGCAACATATCTTAGTTTATCAATATAATAAGGAGTTTCATATGAAGGCACCCGTA  300
     -35                                           -10                              S.D.    m  k  a  p  v

CGGCTGGCGGGGTTACCCGAGCCCGGACAGATCGGTTACAGCCCTCCTCTTCCCGATCGCCGGGGAGATGCTGGGCAAGGACCAGCCCGTGATCCTCC  400
 r  a  v  t  g  a  a  g  q  i  g  y  s  l  t  f  r  i  a  a  g  e  m  l  g  k  d  q  p  v  i  l

AGCTTTTGGAGATCCCCCAGGCCATGAAGGCCCTGGAGGGCGTGGTCATGGAGCTGGAGGACTGCGCCTTCCCCCTGCTTGCGGGCCTCGAGGCCACCGA  500
 q  l  l  e  i  p  q  a  m  k  a  l  e  g  v  v  m  e  l  e  d  c  a  f  p  l  l  a  g  l  e  a  t  d

CGACCCCAAGGTGGCCTTCAAGGACGCCGACTACGCCCTCGTGGGGGCGGCCCCCCGCAAGGCGGGATGAGAGCGGGACCTTTGCAGGTAAAC  600
 d  p  k  v  a  f  k  d  a  d  y  a  l  l  v  g  a  a  p  r  k  a  g  m  e  r  r  d  l  q  v  n

GGCAAGATCTTCACCGAGCAGGGCCGGGCCCTGGCCGAGGTGGCCAAGAAGGACGTCAAGGTGCTGGTGGTGGGCAACCCCGCCAACACCAACGCCCTCA  700
 g  k  i  f  t  e  q  g  r  a  l  a  e  v  a  k  k  d  v  k  v  l  v  v  g  n  p  a  n  t  n  a  l
```

FIG. 4 CONT.

```
TCGCCTACAAGAACGCCCCCGGCCTCAACCCCCGGAACTTCACCGCCATGACCCGGCTGGACCACAACGGGCCAAGGCCCAGCTCGCCAAGAAGACCGG  800
 i  a  y  k  n  a  p  g  l  n  p  r  n  f  t  a  m  t  r  l  d  h  n  r  a  k  a  q  l  a  k  k  t  g

GACGGGGTGGACCGGCATCCGCCGCATGACGCTGTGGGCAACCACTCCTCCACCATGTTCCCCGACCTCTTCCACGCCGAGGTGGACGGCAGGCCCGCC  900
 t  g  v  d  r  i  r  r  m  t  v  w  g  n  h  s  s  t  m  f  p  d  l  f  h  a  e  v  d  g  r  p  a

CTGGAGCTCGTGGACATGGAGTGGTACGAGAAGGTCTTCATCCCCACCGTGGCCCAGCGTGGGGCGGCCATCATCCAGGCCCGGGGGCCAGCAGGCCG  1000
 l  e  l  v  d  m  e  w  y  e  k  v  f  i  p  t  v  a  q  r  g  a  a  i  i  q  a  r  g  a  s  s  a

CCAGCGCCGCGAACGCCGCCATAGAGCACATCCGGGACTGGGCTCTGGGCACCCCGGAGGGGACTGGGTTCCATGCCGTCCCCTCCAAGGGGAGTA  1100
 a  s  a  a  n  a  a  i  e  h  i  r  d  w  a  l  g  t  p  e  g  d  w  v  s  m  a  v  p  s  q  g  e  y

CGGCATCCCCGAGGGCATCGTCTACTCCTTCCCGGTGACGGCCAAGGACGGGGCGTACCGGGTCGTGGAGGGCTGGAGATCAACGAGTTCGCCCGCAAG  1200
 g  i  p  e  g  i  v  y  s  f  p  v  t  a  k  d  g  a  y  r  v  v  e  g  l  e  i  n  e  f  a  r  k

CGCATGGAGATCACGGCCCAGGAACTTCTGGACGAGATGGAGCAGGTGAAGGCCCTGGGCCTCATCTGAGAGGCTGGCCTCAGAGCCCCACCGCCCT  1300
 r  m  e  i  t  a  q  e  l  l  d  e  m  e  q  v  k  a  l  g  l  i  *

GCGGTGGGGCTTTACACCACCCCATGTGCTGGCTTGCGCCAGGCCTCGAGGGCCCAAAAGCTCCCTGGGAGCTTCCCCGGGCCCGTCGGGCGAAGGCA  1400

ACCGGAAGGGTATTAGCCTTTGGGCCAGGCCTCGAGGGCCCAAGGGTAGACCACCCAGGCCGCCGTCTCTCGGCGTAGAAGTCGGGGCGTCCGGCACC  1500
                                                                                                    Hinfl CGGTTCCGCCCGGCTTGAAGTGGAGAGTCGCCCCCCGGCCCCCGCCCGGCCCGGCCCTTCACGGCAAGGCCGTGCCCCCGAGTC  1598
```

EXPRESSION OF POLYPEPTIDES IN E. COLI UNDER CONTROL OF THE E. COLI MDH-GENE PROMOTER

This invention relates to methods for expressing polypeptides in E. coli, and to expression vectors and recombinant DNA molecules useful in such methods. The invention further provides a process for producing polypeptides derived from genes native to the genus Thermus.

Bacteria such as E. coli are widely used as host organisms in processes for the production of foreign polypeptides by recombinant DNA technology. Such processes are particularly useful where desired polypeptides are not easily obtained from their natural source organisms.

In the past, techniques for the cloning and expression of foreign genes in micro organisms have involved construction of recombinant expression vectors comprising the coding sequence of the desired foreign gene under the control of the specific expression mechanisms of the organism into which the vector is to be introduced.

An important element of these expression mechanisms is the promoter. This is a region of DNA located in relatively close proximity to the coding sequence of a structural gene. The promoter is involved in the binding of DNA polymerase to initiate transcription. Selection of a suitable promoter is important in order to obtain efficient expression. In processes where a high level of expression of product polypeptide is required, it is usual to select a strong promoter, i.e. one which can sustain a high rate of transcription.

In the context of expression systems based on E. coli known strong promoters include the naturally occurring lac and trp promoters and the synthetic hybrid tac promoter. In general, these promoters have consensus sequences showing only slight variation from the following:

```
TTGACA———17bp———TATAAT (SEQ ID NO:1 and
 (-35)              (-10)    SEQ ID NO:2)
```

It has been an aim of many researchers to provide additional strong promoters particularly in order to allow expression at high levels in circumstances where use of available promoters is problematical. To this end, promoters such as the tac promoter (a hybrid between the trp and lac promoters) have been constructed.

It is an object of the present invention, according to one aspect thereof to provide a novel expression system for expressing genes (especially, but not exclusively foreign genes) in E. coli.

It has now surprisingly been found that an E. coli gene control sequence which includes a promoter which does not have the consensus sequence shown above can sustain a high rate of transcription.

Thus according to one aspect of the present invention there is provided an expression vector For expressing in E. coli a polypeptide other than E. coli malate dehydrogenase coded for by a DNA coding sequence (particularly a foreign DNA coding sequence), said vector comprising a DNA sequence coding for said polypeptide and including an initiation codon wherein said DNA sequence is operatively linked to a sequence located upstream of the initiation codon and which is capable of controlling expression of said polypeptide, characterised in that said upstream sequence (a) consists of the 285 base pair sequence GCA TGC AAA TTC TGC TTA AAA GTA AAT TAA
TTG TTA TCA AAT TGA TGT TGT TTT GGC TGA
ACG GTA GGG TAT ATT GTC ACC ACC TGT TGG
AAT GTT GCG CTA ATG CAT AAG CGA CTG TTA
ATT ACG TAA GTT AGG TTC CTG ATT ACG GCA
ATT AAA TGC ATA AAC GCT AAA CTT GCG TGA
CTA CAC ATT CTT GAG ATG TGG TCA TTG TAA
ACG GCA ATT TTG TGG ATT AAG GTC GCG GCA
GCG GAG CAA CAT ATC TTA GTT TAT CAA TAT
AAT AAG GAG TTT CAT (SEQ ID NO:3)

or (b) consists of a sequence having a DNA sequence related to that of said upstream sequence (a), said related sequence differing from the specific sequence (a) only to such an extent that expression of said polypeptide is not eliminated.

It is preferred that said related sequence (b) has at least a 50%, preferably a 75%, most preferably 95% sequence homology with sequence (a) above.

Where sequence (b) deviates from the precise sequence (a) such deviation may comprise deletions, insertions, and/or substitutions. To maintain high levels of expression of the polypeptide, it is preferred that only a relatively small number of such deletions, insertions and/or substitutions be made, i.e. not more than 10, most preferably not more than 5. Generally only 1 or 2 such deletions, insertions and/or substitutions should be made.

Although it is preferred that the related sequence (b) has about 285 bases, in view of the possibility for inserting and deleting bases as indicated above, related sequence (b) can if desired vary in length. Preferably it is from 200 to 350 bases in length.

The invention also provides for an expression vector for expressing a polypeptide other than E. coli malate dehydrogenase in E. coli coded for by a gene, particularly a foreign gene, characterised in that said vector comprises (1) a DNA sequence capable of controlling expression of said polypeptide, selected from sequences (a) and (b) as defined above, and (2) a restriction enzyme site arranged in relation to said sequence (a) or (b) so as to allow the introduction of a DNA coding sequence which codes for said gene into the expression vector, whereby said coding sequence is operatively linked to sequence (a) or (b) enabling expression of the polypeptide.

It is preferred that the restriction enzyme site referred to is the NdeI site having the the sequence CATATG (SEQ ID NO:4). This site may be provided by linking a DNA sequence having a 5'sequence starting ATG ... immediately adjacent the 3'-terminal ... CAT of sequence (a) set forth above. Alternatively, if the expression vector includes a related sequence (b), it is preferred that the related sequence has a 3'-terminal sequence ... CAT which can be linked to an ATG to provide an NdeI site.

According to a further aspect of the present invention there is provided a process for expressing a polypeptide in E. coli comprising culturing a host strain of E. coli transformed with an expression vector as defined in accordance with the first aspect of the invention.

It is further preferred that when the expression vector of the invention comprises related sequence (b) defined above, said related sequence includes at least one of the following control elements:

(i) a promoter (ii) a catabolite repression site (iii) a ribosome binding site

Said related sequence preferably include at least two, most preferably three of expression control elements (i) to (iii) above. (It is to be understood that sequence (a) includes all three of the aforementioned control sequences).

The specific sequence;

TTGTAAACGGCAATTTTGTGGATTAAGGT (SEQ ID NO:5)

contained within sequence (a) above corresponds to the 35 base pairs identified as comprising the E. coli mdh promoter.

Preferably the related sequences (b) referred to above would normally have a high degree of homology to this specific sequence. Thus, where expression vectors according to the invention comprise a promoter having a sequence which is related to the aforementioned specific sequence it is preferred that the promoter has at least a 50%, preferably at least 75%, most preferably at least 95% sequence homology with the specific sequence of the *E. coli* mdh gene promoter.

Thus preferably the promoter is composed of from 12 to 50 bases, most preferably 20 to 35 bases. The promoter is desirably composed of about 29 bases.

Any deviations from the precise sequence indicated above may comprise deletions, insertions and/or substitutions of one or more bases. To avoid loss of activity as a promoter, it is preferred that only a relatively small number of such deletions, insertions and/or substitutions be made, i.e. not more than 10, most preferably not more than 5. Generally only 1 or 2 such deletions, insertions and/or substitutions should be made.

It is further preferred that the promoter has a base sequence comprising the sequence TTGTAA (SEQ ID NO:6) at the 5' end and the sequence TAAGGT (SEQ ID NO:7) at the 3' end. Alternatively the promoter may have a base sequence comprising the sequence TGGAAT (SEQ ID NO:8) at the 5' end and the sequence AATGTT (SEQ ID NO:9) at the 3' end.

In addition to the preferred terminal sequences indicated above, it is also preferred that the promoter has an intervening sequence selected from the sequence

ACGGCAATTTTGTGGAT (SEQ ID NO:10)

and related sequences differing from the aforementioned sequence only to such an extent that activity as a promoter is essentially retained. Any deviations from the precise sequence indicated above may comprise deletions insertions and/or substitutions of one or more bases. To avoid loss of activity as a promoter, it is preferred that only a relatively small number of such deletions, insertions and/of substitutions be made i.e. not more than 10, most preferably not more than 5. Generally only 1 or 2 such deletions, insertions and/or substitutions should be made.

In its most preferred form, the promoter of the vector of the present invention has the sequence:

TTGTAAACGGCAATTTTGTGGATTAAGGT (SEQ ID NO:5)

In a particular embodiment of the invention an expression vector for expressing in *E. coli* a polypeptide other than *E. coli* malate dehydrogenase coded for by a DNA coding seqence comprises (1) an *E. coli* mdh gene promoter having the sequence,

TTGTAAACGGCAATTTTGTGGATTAAGGT (SEQ ID NO:5)

or a promoter having a DNA sequence related to that of the *E. coli* mdh gene promoter, said related sequence differing from the specific sequence only to the extent that activity as a promoter is essentially retained and (2) a restriction enzyme site arranged in relation to said promoted so as to allow introduction of the DNA coding sequence into the vector whereby said coding sequence is operatively limited to the promoter.

Such an expression vector is of advantage for use in construction of expression vectors according to the invention suitable for expressing a desired polypeptide in *E. coli*.

In a further embodiment the vector comprises the DNA coding sequence operatively linked to the promoter and the promoter is capable of controlling expression of the polypeptide.

A vector according to the invention is plasmid pMTL1005, deposited at NCIMB, 23 St Machar Drive, Aberdeen, Scotland, UK, on 12 Oct. 1992 under deposit reference no. NCIMB-40520.

The construction of pMTL1005 and the construction of further vectors according to the invention comprising the *E. coli* mdh promoter is described hereinafter.

According to another aspect of the present invention there is provided a recombinant DNA molecule comprising a DNA coding sequence and including an initiation codon operatively linked to a sequence upstream of the initiation codon, characterised in that the DNA coding sequence codes for a polypeptide other than *E. coli* malate dehydrogenase and said upstream sequence (a) consists of the 285 base pair sequence GCA TGC AAA TTC TGC TTA AAA GTA AAT TAA
TTG TTA TCA AAT TGA TGT TGT TTT GGC TGA
ACG GTA GGG TAT ATT GTC ACC ACC TGT TGG
AAT GTT GCG CTA ATG CAT AAG CGA CTG TTA
ATT ACG TAA GTT AGG TTC CTG ATT ACG GCA
ATT AAA TGC ATA AAC GCT AAA CTT GCG TGA
CTA CAC ATT CTT GAG ATG TGG TCA TTG TAA
ACG GCA ATT TTG TGG ATT AAG GTC GCG GCA
GCG GAG CAA CAT ATC TTA GTT TAT CAA TAT
AAT AAG GAG TTT CAT (SEQ ID NO:3)

or (b) consists of a sequence having a DNA sequence related to that of said upstream sequence (a), said related sequence differing from the specific sequence (a) only to such an extent that expression of said polypeptide is not eliminated.

In the course of the investigations which led to the construction of the expression vectors referred to above it was surprisingly found that high levels of expression of the malate delydrogenase enzyme from thermophilic bacteria of the genus Thermus can be achieved in *E. coli*, by expression under the control of an *E. coli* gene promoter.

Thermus spp. are described as Gram-negative, non-sporulating, nonotile, aerobic, rods/filaments (Brock, & Freeze, 1969) and are found in natural thermal springs with an optimum laboratory growth temperature of between 70° to 80° C. (Brock, 1978). As extreme thermophiles, Thermus spp. synthesise proteins and enzymes that are not only heat stable but also resistant to chemical denaturants including organic solvents and high concentrations of urea and detergents (Iijima et al., 1984; Smith and Sundaram, 1988). This has generated a great deal of interest in the thermostable enzymes of Thermus spp. a number of which have been purified and characterised.

Malate dehydrogenase (MDH) catalyses the interconversion of malate and oxaloacetate as part of the tricarboxylic acid cycle using $NAD^+/NADH$ as a cofactor. The dimeric, mitochondrial and cytosolic isozymes from mammalian eukaryotic sources are extremely well characterised in terms of enzyme kinetics, mechanism and three-dimentional X-ray structure (Birktoft and Banaszak, 1984). The nucleotide sequence of the mdh gene from *T. aquaticus* B has been determined (Nicholls et al., 1990) and the predicted amino acid sequence of the polypeptide was found to be identical with that for the *T. flavus* enzyme (Nishiyama et al., 1986). *T. aquaticus* B MDH was found to share a high degree of amino acid sequence identity with the porcine cytosolic enzyme for which the X-ray structure has been determined at 1.8 Å resolution (Birktoft et al., 1987). This allowed molecular modelling of a dimeric *T. aquaticus* B MDH tertiary structure based on the coordinates For porcine cytosolic MDH (Duffield et al., 1990). Prior to the making of the present invention, a need existed to improve the level of expression in *E. coli* of the *T. aquaticus* mdh gene especially in order to investigate, by protein engineering, the characteristics of *T. aquaticus* MDH, in particular its high degree of protein thermostability.

However, attempts at expression of Thermus spp. genes in mesophilic hosts such as *E. coli* have up to now resulted in poor expression only (Tanaka et al., 1981; Iijma et al., 1986; Nicholls et al 1990). The reasons for this are unclear, however, several structural genes from Thermus spp. have been cloned and sequenced and were found to have a very high (70%) G/C content (Kagawa et al., 1984; Kunai et al., 1986; Nishiyama et al., 1986) resulting in a marked preference (approximately 95%) for G or C in the third position of degenerate codons. Consequently there is a non-optimum codon usage pattern in terms of the corresponding tRNA population of *E. coli* which may be one reason for poor expression.

It has now been found that high levels of expression of Thermus spp. genes can be achieved in *E. coli* by the use of recombinant expression vectors comprising a Thermus spp DNA coding sequence operatively linked to *E. coli* gene transcription and translation initiation signals.

The present invention thus further provides a process for producing a polypeptide by expressing a DNA coding sequence which is native to the genus Thermus or which is related to said native sequence which comprises culturing a transformed micro organism of the species *E. coli*, characterised in that said transformed micro organism includes a plasmid comprising said DNA sequence operatively linked to a promoter which is an *E. coli* promoter or a promoter having a DNA sequence related to the sequence of an *E. coli* promoter, said related sequence differing from the specific sequence of an *E. coli* promoter only to such an extent that activity as a promoter is essentially retained and that said polypeptide is expressed such that it forms preferably greater than 35% soluble cell protein, e.g., between 35 and 90% soluble cell protein, more preferably between 40 and 55% and most preferably about 50% soluble cell protein.

The aforementioned related DNA coding sequence may differ from the sequence of a DNA coding sequence which is native to the genus Thermus by one or more deletions, insertions and/or substitutions.

The stated DNA coding sequences preferably code for native Thermus polypeptides, but the invention also includes processes in which polypeptides differing from native Thermus proteins are produced, e.g. polypeptides differing from native ones in not more than 10, preferably not more than 5 amino acid residues.

Particularly high levels of expression are obtained by replacing the usual initiation codon (GTG) of Thermus coding sequences by the codon ATG, thus it is preferred that the DNA coding sequence has an initiation codon with the sequence ATG.

The stated promoter sequence preferably is as defined above in connection with the first aspect of the invention. Thus, in the process of the invention, where a promoter has a sequence which is related to the aforementioned *E. coli* promoter it is preferred that the promoter has at least a 50%, preferably 75%, most preferably 95% sequence homology with the sequence of an *E. coli* gene promoter.

Thus preferably the promoter is composed of from 12 to 50 bases most preferably 20 to 35 bases. The promoter is most preferably composed of about 29 bases.

It is also preferred that the promoter has a base sequence comprising the sequence TTGACA at the 5' end and the sequence TTAACT (SEQ ID NO:11) at the 3' end. Alternatively, it is preferred that the promoter has a base sequence comprising the sequence TCAATT (SEQ ID NO:12) at the 5' end and the sequence ACAGTT (SEQ ID NO:13) 3' end.

It is further preferred that the stated DNA coding sequence, coding for Thermus proteins and proteins related thereto as defined above is operatively linked to a ribosome binding site. Surprisingly it has been found that although it is desirable to include a ribosome binding site having a moderate dgree of homology with the consensus sequence

5' TAAGGAGGTGXXX 3' (SEQ ID NO:14)

wherein X can be adenine, guanine, cytosine or thymine (which is based on the 3'-end of rRNA) higher levels of expression have been obtained using sequences which deviate by 2 or more base changes than using sequences which deviate by only one base change from the consensus sequence.

This is apparent from the table below which compares levels of expression obtainable using three different sequences derived from Thermus and *E. coli* sequences.

|  |  | Expression |
|---|---|---|
| Consensus | T A A G G A G G T G X X X A T G |  |
| *Engineered Thermus mdh | a A A G G A G G T G c a t A T G | 2% (SEQ ID NO: 15) |
| **Engineered *E Coli* mdh | T A A G G A G t T t c a t A T G | 47% (SEQ ID NO: 16) |
| ***Engineered lacz | a c A G G A a a c a c a t A T G | 49% (SEQ ID NO: 17) |

\* = pRMA5
\*\* = pRMA102
\*\*\* = pRMA51

DESCRIPTION OF FIGURES

The invention will now be described in more detail with particular reference to the accompanying figures of which.

The following example illustrates a method for the expression of foreign polypeptides in *E. coli* regulated by the *E. coli* mdh gene promoter, and the use of *E. coli* promoters generally for the expression of polypeptides native to the genus Thermus in *E. coli*.

EXAMPLE

Bacterial strains and vectors

*E. coli* TG-2 ((lacIP$^q$ δM15-pro), supE, thi, hsdD5/F', traD36, proA$^+$B$^+$, recA) was used as the host strain for all recombinant plasmids and grown routinely in 2xTY medium at 37° C. in the presence of 100 μg/ml ampicillin when required. The plasmid vector pKK223-3 was obtained from Pharmacia, and M13mt122 and pMTL1003 were kindly provided by Dr S. Chambers.

DNA manipulation

Standard recombinant DNA techniques were performed as described in Maniatis et al., (1982). For nucleotide sequencing the dideoxy-chain termination reaction was employed (Sanger et al., 1977) using deoxy-7-deazaguanosine at 50° C. (Miusawa et al., 1986). Oligonucleotide site-directed mutagenesis was performed using the primer extension method (Gillam and Smith 1978). The mutagenic oligonucleotide (5'-AGGAGGTGGCATATGAAGGCAC-3') (SEQ ID NO:18) was synthesised using an Applied Biosystems 380A DNA synthesiser.

Enzyme and protein assays

Enzyme activity was measured as described previously (Smith et al., 1982). Protein concentration was determined by the "Biuret" method (Gornall et al., 1949). Expression was estimated as a percentage of soluble cell protein by using the equation:

$$\frac{\text{specific activity of pure MDH (U/mg)} \times 100}{\text{specific activity of extract (U/mg)}}$$

where the specific activity of pure MDH=190 U/mg (Alldread et al., 1991—to be submitted for publication). Crude cell extracts were heat treated at 70° C. for 30 min.

Electrophoresis

Proteins were analysed by SDS-polyacrylamide gel electrophoresis (SDS-Page) using the "Phastgel" system (Pharmacia).

Generation of Recombinant Expression Plasmids

Figure 1:
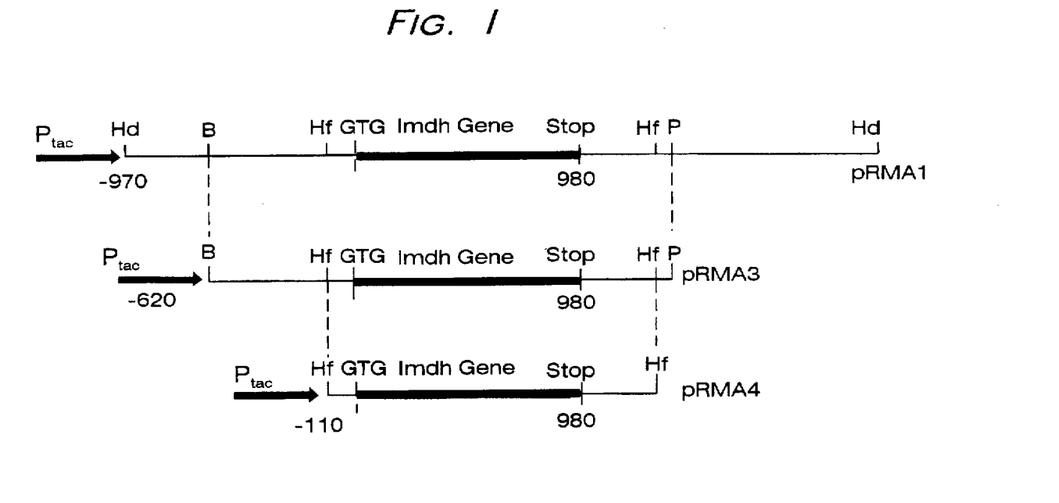
FIG. 1 is a representation of the cloning strategy used to generate the recombinant plasmids pRMA1-4.

The *T. aquaticus* mdh gene was initially cloned as part of a 3.2 kb Hind III fragment and the entire nucleotide sequence determined (Nicholls et al., 1990). The 3.2 kb Hind III fragment was ligated into the Hind III site of pKK223-3 in both orientations to generate the recombinant plasmids pRMA1 and pRMA2 respectively. A 2.0 kb BamHI/PstI fragment, containing the mdh gene, was isolated and ligated into the linker BGmHI and PstI sites of the plasmid vector pKK223-3 to generate the recombinant plasmid pRMA3 (FIG. 1). The fragment containing the mdh gene was further reduced to 1.4 kb by excision with HinfI (FIG. 1), blunt-ended and ligated into the Sma I site of pUC9 to allow for blue white selection of recombinant plasmids. The 1.4 kb fragment containing the gene was excised from pUC9 with EcoRI and HindIII then ligated into the corresponding sites of pKK223-3 and designated pRMA4 (FIG. 1).

Insert DNA from pRMA4 was subcloned into M13mt122 as a 0.5 kb EcoRI/AatII fragment to generate single stranded DNA for site directed mutagenesis. Using a 22 mer mutagenic oligonucleotide (5'GGAGGTGGCATATGAAGGCAC-3') (SEQ ID NO:19) a NdeI site (5'-CATATG-3') was created which incorporated the initiation codon (FIG. 2) of the Thermus mdh gene. The entire nucleotide sequence of the mutated 0.5 kb EcoRI/AGtII fragment was determined to check for other undesirable mutations which may have been introduced. The 0.5 kb EcoRI/AatII fragment of pRMA4 was replaced by the mutated 0.5 kb EcoRI/AatII fragment to generate pRMA41. The 1.4 kb EcoRI/HindIII fragment containing the engineered *T. aquaticus* mdh gene was taken from PRMA41, blunt-ended with T4 DNA polymerase, and ligated into the SmaI site of pMTL1003. A recombinant plasmid was identified with the *T. aquaticus* mdh gene in the correct orientation for expression from the vector trp promoter and was designated pRMA5. A 0.1 kb NdeI fragment was deleted from pRMA5 to reduce the insert 5' flanking sequence to a minimum and to insert the gene behind a consensus *E. coli* type ribosome binding site. The resultant plasmid was designated pRMA51 (FIG. 3).

Figure 3:
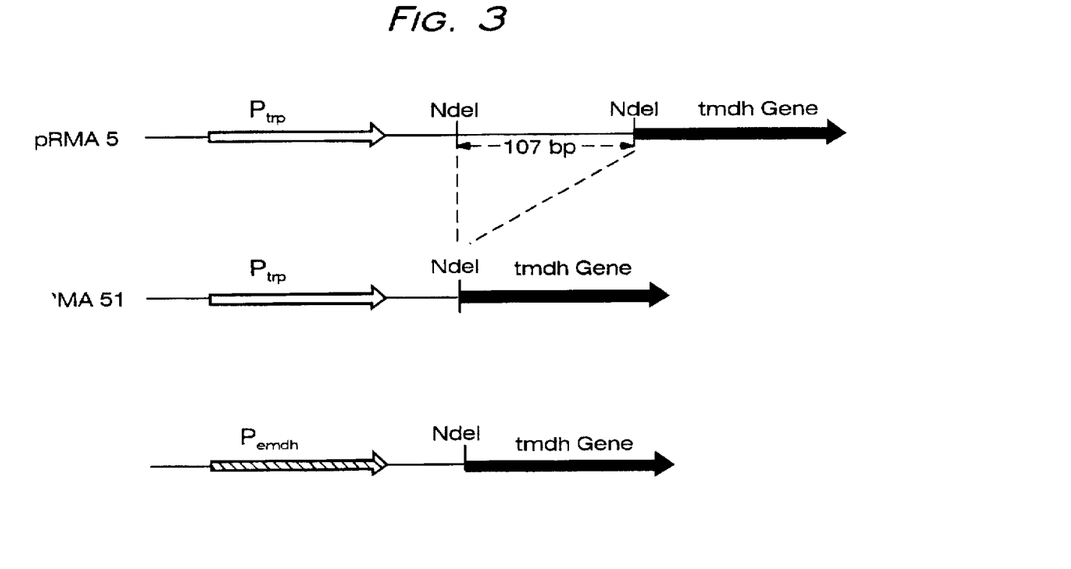
FIG. 3 is a representation of the cloning strategy used to generate the recombinant plasmids pRMA51 and pRMA102. Abbreviations: Ptrp, trp transcription promoter; Pemdh, *E. coli* transcription promoter; tmdh, *T. aquaticus* mdh gene.
Figure 4:
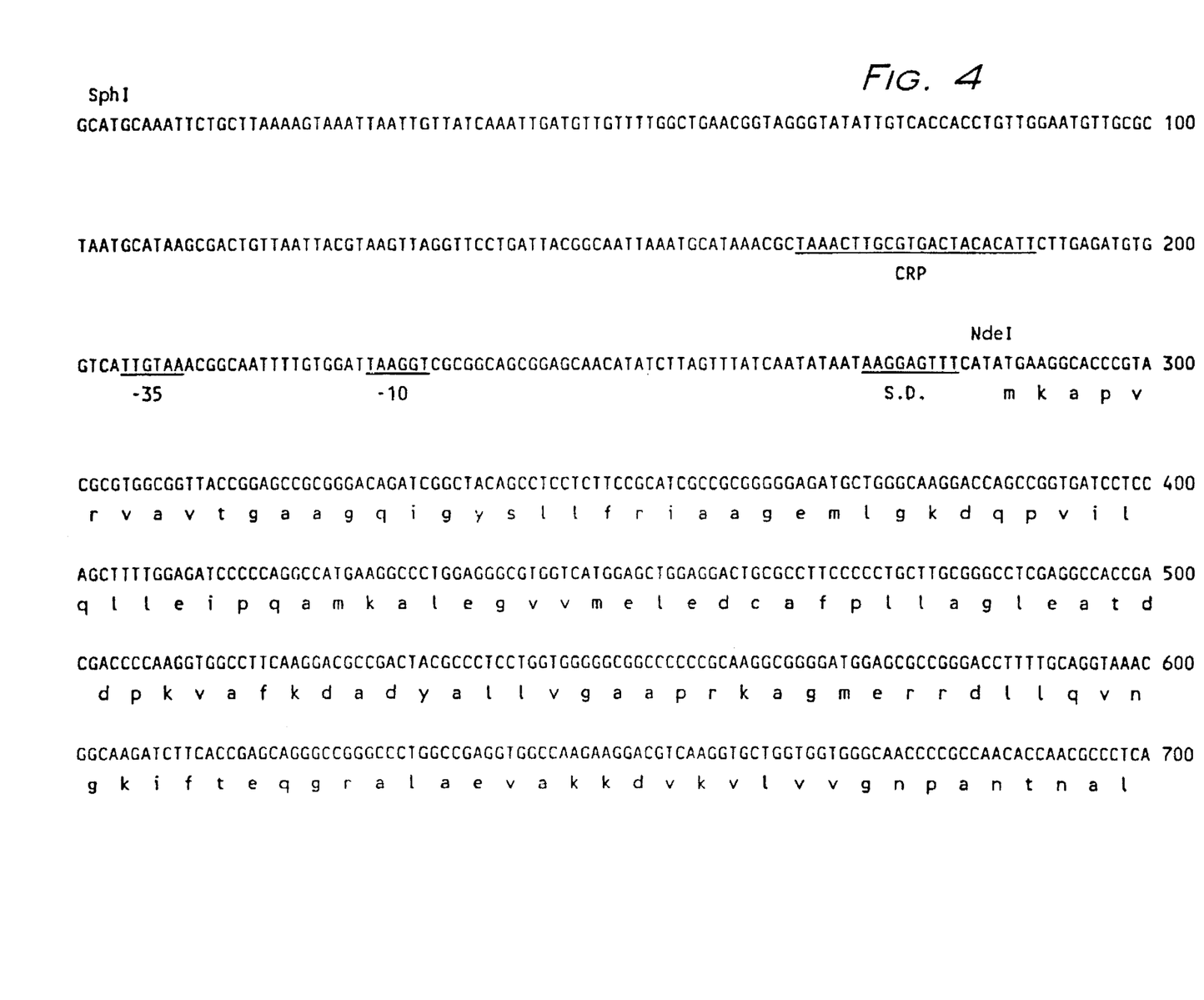
FIG. 4 is the nucleotide sequence of the *E. coli* mdh gene transcription and translation initiation signals fused to the *T Aquaticus* mdh gene. The predicted amino acid sequence for *T. aquaticus* MDH is shown below the nucleotide sequence, the termination codon is denoted by an asterisk (*). The putative *E. coli* ribosome binding site (S.D.), transcription initiation signals (−10 and −35 and CRP binding site (CRP) are shown underlined (SEQ ID NOS:24 and 25).

A 1.0 kb SphI/KpnI fragment, containing the *E. coli* mdh promoter and part of the gene was excised from pDN4 (Nicholls et al., 1989) and ligated into M13mt122 SphI/KpnI sites. Site-directed-mutagenesis was performed using a 21 mer oligonucleotide (5'-AGGAGGTGGCATATGAAGGCAC-3') (SEQ ID NO:18) to create a NdeI site incorporating the initiating codon of the *E. coli* mdh gene. The mutated SphI/Kpni fragment was confirmed by DNA sequencing then ligated into pDN4 cut with SphI/KpnI to recreate pDN4 containing a NdeI site. This recombinant plasmid was designated pRMA10. A 1.9 kb SphI/SalI fragment, containing the *E. coli* mdh gene and promoter was excised from pRMA10, blunt ended and ligated into the PvuII site of pMTL28P (Nicholls et al 1989) to generate pRMA101. The *E. coli* mdh gene coding sequence was removed from pRMA101 as a 1.7 kb NdeI/HindIII fragment and replaced with the Thermus mdh gene coding sequence (taken from pRMA41) as a similar 1.3 kb NdeI/HindIII fragment to generate pRMA102. In this way the Thermus mdh gene was placed under the control of the *E. coli* mdh promoter and ribosome binding site in pRMA102 (FIG. 3 and FIG. 4).

Expression of *T. aquaticus* MDH from the recombinant plasmids

For all the recombinant plasmids in *E. coli* TG-2 the expression levels of *T. aquaticus* MDH were estimated, on the basis of specific activities, as a percentage of soluble protein in both crude and heat treated cell extracts (Table 1). The original *T. aquaticus* mdh gene cloned into pMTL22P, as a 3.2 kb Hind III fragment, was found to express thermostable MDH at 0.4% of the soluble cell protein. Thermostable MDH was estimated to constitute 0.1% soluble cell protein of *E. coli* TG-2 containing pRMA1 and was not expressed from pRMA2 (Table 1). This result suggests that expression of the *T. aquaticus* mdh gene is directed by the pKK223-3 transcription promoter and is in agreement with the result obtained using pMTL22P as a vector (Nicholls et al., 1989). The reduced expression observed in the pKK223-3 vector system is probably due to the higher copy number and enhanced stability of the pMTL vector series (Chambers et al., 1988).

Expression from the recombinant plasmids pRMA1-4 was found to exhibit an inverse relationship with respect to fragment size (Table 1). This is consistent with the *B. stearothermophilus* lct gene when cloned into pKK223-3, where a reduction of insert DNA size was correlated with an increase in expression (Barstow et al., 1986). The reason for this observation is unclear but may be due to an increase in plasmid copy number of stability. Alternatively, the increase in expression may reflect an enhancement in transcription efficiency either by a kinetic advantage in production of shorter mRNA species or by deletion of inhibitory DNA sequences. There are four, two and one putative stem loop structures occurring 5' to the initiation codons of pRMA1, pRMA3, and pRMA4 respectively.

Engineering a NdeI site and alteration of translation intiation codon.

Figure 2:
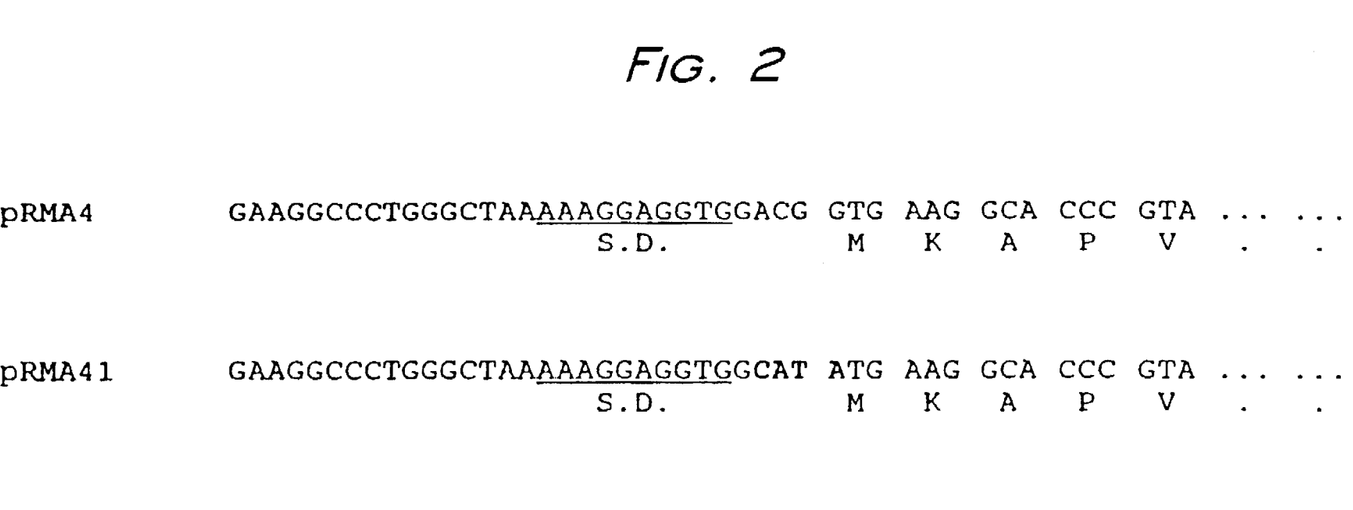
FIG. 2 is the DNA sequence about the initiation codon of the *T. aquaticus* mdh gene in pRMA4 and pRMA41. Putative Shine-Dalgarno sequence is underlined and denoted S.D. Bases changed by site directed mutagenesis are shown in bold type in pRMA41. The predicted N-terminal amino acid sequence is shown beneath the DNA sequence (SEQ ID NO:20, 21, 22, and 23).
Figure 5:
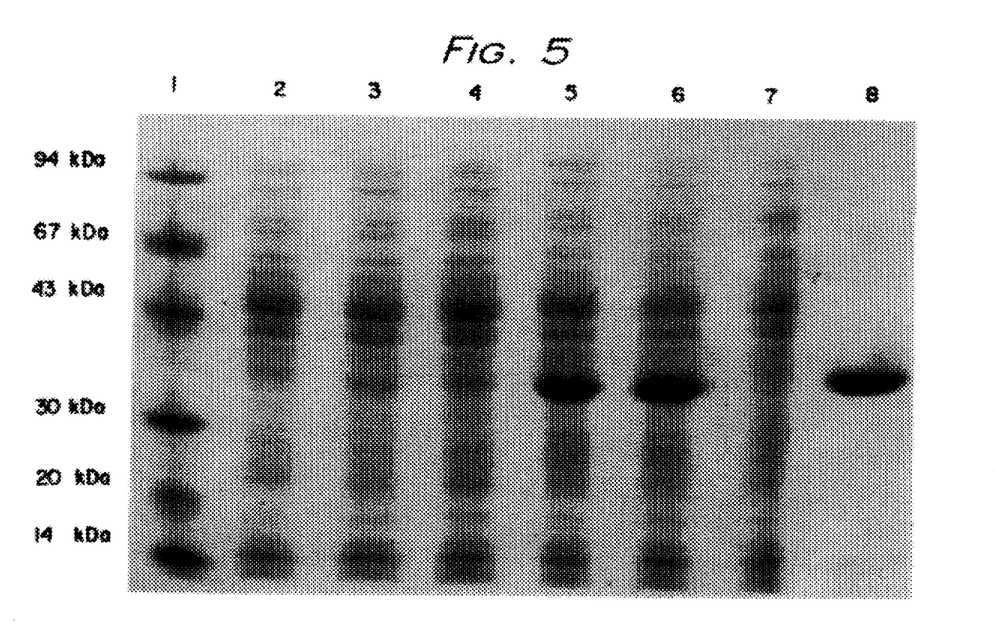
FIGS. 5 and 6 are respectively SDS-page of crude and heated cell extracts from pRMA1, pRMA4, pRMA41 and pRMA51.
Figure 6:
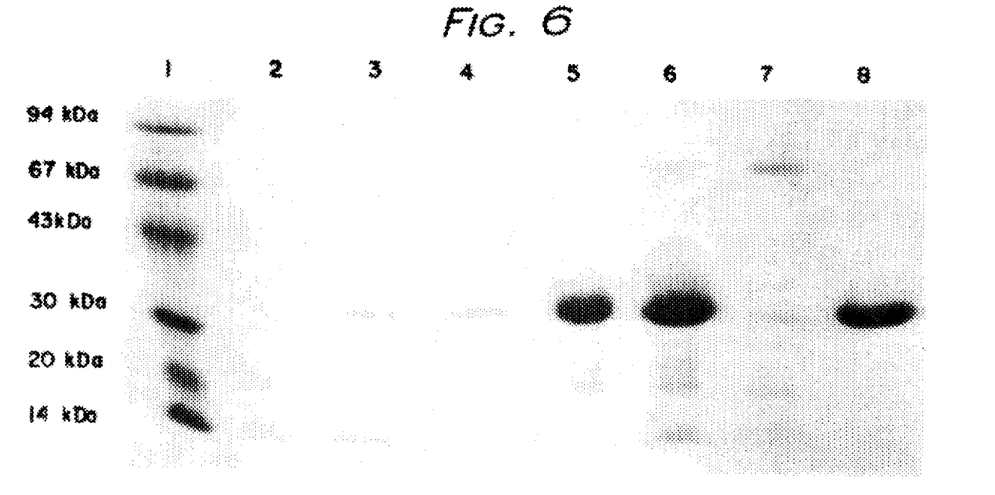

The only difference between pRMA4 and pRMA41 was four contiguous base pairs, one of which altered the translation initiation codon from GTG to ATG (FIG. 2). There was about an eight fold increase in expression of *T. aquati-* cus MDH from pRMA41 when compared to pRMA4 (Table 1 and FIG. 5). *T. aquaticus* MDH was expressed from pRMA5 at a slightly lower level than from pRMA41 (Table 1) possibly because of a minor difference in either plasmid copy number or strength of transcription promoter between the two vectors.

*T. aquaticus* MDH was expressed at a very high level from pRMA51 in which the mdh gene was operatively linked to the *E. coli* trp promoter. The same high level of expression was observed using pRMA102 in which the mdh gene was operatively linked to the *E. coli* mdh gene promoter. In both cases *T. aquaticus* MDH was expresseed as approximately 50% soluble cell protein (Table 1 and FIG. 5).

It can be seen from the results presented herein that expression of the *T. aquaticus* malate dehydrogenase gene in *E. coli* was increased by using site-directed mutagenesis in accordance with the invention. Initially, expression of the gene was at a relatively low level (0.1% soluble cell protein) and was effected by read through from the vector lac Z gene promoter. A small enhancement in expression was achieved by subcloning to reduce the amount of DNA down-stream of the lac Z promoter and 5' to the initiation codon. A NdeI restriction enzyme site (5'-CATATG-3') was engineered to include the initiation codon which was changed from GTG to ATG. This gave an eight fold increase in expression corresponding to 3.2% soluble cell protein in a crude cell extract. Expression was further increased by subcloning, via the engineered NdeI site, into two plasmid expression vectors: one based on the *E. coli* trp promoter and the other using the *E. coli* mdh promoter. For both expression systems a level of 40–50% soluble cell protein was achieved. Heat treatment of the crude cell extract gave a further purification of Thermus MDH to over 90% soluble cell protein.

Although the theoretical basis for the benefits obtained according to the invention is not entirely clear, it is presently believed that it may be initiation of translation that limits expression of *T. aquaticus* MDH in *E. coli*.

Construction of pMTL1005

The *E. coli* mdh gene and promoter, containing the NdeI site engineered at the start codon, was excised from pRMA10 as a 1.9 kb SphI/EcoRI restriction fragment. This was ligated between the SphI and EcoRI sites of pMTL21P (Chambers et al., 1988) to generate pRMA1021. The plasmid pRMA1021 has a unique HindIII site close to the 5' end of the *E. coli* mdh gene promoter sequence. pRMA1021 was first digested with HindIII, then blunt-ended using klenow DNA polymerase. Enzyme activities were removed by phenol extraction and the blunt-ended fragment was then digested with NdeI. Following agarose gel elecrophoresis a 0.3 kb fragment was isolated which contained the entire *E. coli* mdh gene promoter flanked by blunt-HindIII site and a NdeI cohesive end. The vector pMTL1000 (Brehm et al., 1992) was digested with PvuII and NdeI to remove the lacZ gene promoter and the vector backbone isolated following agarose gel electrophoresis. The 0.3 kb blunt-HindIII/NdeI fragment, containing the *E. coli* mdh gene promoter, was then ligated into the pMTL1000 vector backbone using the compatible PvuII and NdeI sites to generate pMTL1005. Thus, the lacZ gene of pMTL1005 is expressed from the *E. coli* mdh gene promoter and ribosome binding site. Accordingly, pMTL1005 gives rise to blue colonies when transformed into an appropriate. *E. coli* host and plated out in the presence of X-gal as a chromogenic substrate.

Construction of vectors for expression of polypeptides in *E. coli*

The plasmid pMTL1005 can be used as the starting material for manufacture of Further plasmids according to the invention for expression of desired polypeptides in *E. coli*. This may be achieved by a method comprising the following steps:

(1) identify a target gene encoding a desired polypeptide, (2) engineer an NdeI restriction site into the target gene so that the NdeI site includes the ATG start codon of the target gene encoding the desired polypeptide, (3) engineer a further restriction site (not NdeI) into the target gene downstream of the open reading frame of the target gene so as to match one of the restriction sites in the linker region contained in the LacZ gene of pMTL1005, (4) digest pMTL1005 with NdeI and a restriction endonuclease producing the further restriction site referred to in (3) above, then treat with alkaline phosphatase, (5) digest the target gene with NdeI and a restriction endonuclease producing the further restriction site referred to in (3) above, (6) ligate the target gene into the digested pMTL1005 (e.g. by mixture of the products of (4) and (5)), forming a pMTL1005 derived plasmid, (7) transform the ligation mixture into a suitable *E. coli* host strain, and (8) isolate recombinant pMTL1005 derived clones expressing the desired polypeptide.

Recombinant pMTL1005 derived clones in which DNA, possibly the target gene, has ligated into pMTL1005 may be identified as colourless colonies on plates containing ampicillin and X-gal. The desired polypeptide may then be recovered by growing in 2xYT broth containing ampicillin for 16 hours and checking for overexpression of desired polypeptide.

As described above, a vector pMTL1005 was used to generate two independent *E. coli* recombinant clones containing the genes encoding Protein G and Protein L respectively. In crude cell extracts of these recombinant clones. Protein G was estimated to constitute about 25% soluble cell protein and Protein L was estimated to constitute about 15% soluble cell protein.

TABLE 1

Expression of *T. aquaticus* mdh determined on the basis of specific activity.

| Plasmid | Percentage soluble cell proteins | | insert fragment size (kb) |
|---|---|---|---|
| | Crude extract | Heated extract | |
| pRMA1 | 0.25 | | 3.2 |
| pRMA2 | 0.0 | | 3.2 |
| pRMA3 | 0.4 | | 2.0 |
| pRMA4 | 0.8 | | 1.4 |
| pRMA41 | 5.0 | | 1.4 |
| pRMA5 | 4.0 | | 1.4 |
| pRMA51 | 50.0 | | 1.3 |
| pRMA102 | 50.0 | | 1.3 |

We claim:

1. An expression vector for expressing in *E. coli* a polypeptide other than *E. coli* malate dehydrogenase coded for by a DNA coding sequence, said vector comprising a DNA sequence coding for said polypeptide and including an initiation codon wherein said DNA sequence is operatively linked to an upstream sequence located upstream of the initiation codon and which is capable of controlling expression of said polypeptide, wherein said upstream sequence consists of the 285 base pair sequence GCA TGC AAA TTC TGC TTA AAA GTA AAT TAA
TTG TTA TCA AAT TGA TGT TGT TTT GGC TGA
ACG GTA GGG TAT ATT GTC ACC ACC TGT TGG
AAT GTT GCG CTA ATG CAT AAG CGA CTG TTA
ATT ACG TAA GTT AGG TTC CTG ATT ACG GCA
ATT AAA TGC ATA AAC GCT AAA CTT GCG TGA
CTA CAC ATT CTT GAG ATG TGG TCA TTG TAA
ACG GCA ATT TTG TGG ATT AAG GTC GCG GCA
GCG GAG CAA CAT ATC TTA GTT TAT CAA TAT
AAT AAG GAG TTT CAT (SEQ ID NO:3), and wherein if the initiation codon the DNA sequence is not ATG it is changed to ATG.

2. An expression vector for expressing in *E. coli* a polypeptide other than *E. coli* malate dehydrogenase coded for by a gene characterised in that said vector comprises (1) a DNA sequence capable of controlling expression of said polypeptide, selected from said 285 base pair sequence as defined in claim 1, and (2) a restriction enzyme site arranged in relation to said 285 base pair sequence so as to allow the introduction of a DNA coding sequence which codes for said gene into the expression vector, whereby said coding sequence is operatively linked to said 285 base pair sequence enabling expression of the polypeptide, and wherein if the initiation codon of the DNA sequence is not ATG it is changed to ATG.

3. An expression vector according to claim 2 wherein said restriction enzyme site has the sequence CATATG (SEQ ID NO:4).

4. An expression vector according to claim 2 further comprising the DNA coding sequence which has been introduced into the vector.

5. A process for expressing a polypeptide comprising culturing a host strain of *E. coli* transformed with an expression vector as defined in claim 1.

6. An expression vector for expressing in *E. coli* a polypeptide other than *E. coli* malate dehydrogenase coded for by a DNA coding sequence, said vector comprising a DNA sequence coding for said polypeptide and including an initiation codon wherein said DNA sequence is operatively linked to an upstream sequence located upstream of the initiation codon and which is capable of controlling expression of said polypeptide, wherein said upstream sequence is a variant of the 285 base pair sequence GCA TGC AAA TTC TGC TTA AAA GTA AAT TAA
TTG TTA TCA AAT TGA TGT TGT TTT GGC TGA
ACG GTA GGG TAT ATT GTC ACC ACC TGT TGG
AAT GTT GCG CTA ATG CAT AAG CGA CTG TTA
ATT ACG TAA GTT AGG TTC CTG ATT ACG GCA
ATT AAA TGC ATA AAC GCT AAA CTT GCG TGA
CTA CAC ATT CTT GAG ATG TGG TCA TTG TAA
ACG GCA ATT TTG TGG ATT AAG GTC GCG GCA
GCG GAG CAA CAT ATC TTA GTT TAT CAA TAT
AAT AAG GAG TTT CAT (SEQ ID NO:3),
wherein said variant has 95% homology with said 285 base pair sequence, and wherein if the initiation codon of the DNA sequence is not ATG it is changed to ATG.

7. An expression vector for expressing in *E. coli* a polypeptide other than *E. coli* malate dehydrogenase coded for by a DNA coding sequence, said vector comprising a DNA sequence coding for said polypeptide and including an initiation codon wherein said DNA sequence is operatively linked to an upstream sequence located upstream of the initiation codon and which is capable of controlling expression of said polypeptide, wherein said upstream sequence is a variant of the 285 base pair sequence GCA TGC AAA TTC TGC TTA AAA GTA AAT TAA
TTG TTA TCA AAT TGA TGT TGT TTT GGC TGA
ACG GTA GGG TAT ATT GTC ACC ACC TGT TGG
AAT GTT GCG CTA ATG CAT AAG CGA CTG TTA
ATT ACG TAA GTT AGG TTC CTG ATT ACG GCA
ATT AAA TGC ATA AAC GCT AAA CTT GCG TGA
CTA CAC ATT CTT GAG ATG TGG TCA TTG TAA
ACG GCA ATT TTG TGG ATT AAG GTC GCG GCA
GCG GAG CAA CAT ATC TTA GTT TAT CAA TAT
AAT AAG GAG TTT CAT (SEQ ID NO:3),
wherein said variant sequence differs from said 285 base pair sequence by between 1 and 10 deletions, insertions and/or substitutions, and wherein if the initiation codon of the DNA sequence is not ATG it is changed to ATG.

8. An expression vector according to claim, 7 wherein said variant sequence differs from said 285 base pair sequence by not more than 5 deletions, insertions and/or substitutions.

9. An expression vector according to claim 8 wherein said variant sequence differs from said 285 base pair sequence by not more than 2 deletions, insertions and/or substitutions.

10. An expression vector according to claim 7 wherein said variant sequence includes at least one of the following expression control elements;

(i) a promoter (ii) a catabolite repression site (iii) a ribosome binding site.

11. An expression vector according to claim 10 wherein said variant sequence includes at least two of said expression control elements (i) to (iii).

12. An expression vector according to claim 10 wherein said promoter (i) has a base sequence comprising the sequence TTGTAA (SEQ ID NO:6) at the 5' end and the sequence TAAGGT (SEQ ID NO:7) at the 3' end.

13. An expression vector according to claim 12 wherein said promoter (i) has an intervening sequence located between said sequence at the 3' end and said sequence at the 5' end, said intervening sequence being

ACGGCAATTTTGTGGAT (SEQ ID NO:10).

14. An expression vector according to claim 13 wherein the intervening sequence differs from the sequence ACGGCAATTTTGTGGAT(SEQ ID NO:10) by not more than 10 deletions, insertions and/or substitutions.

15. An expression vector according to claim 14 wherein the intervening sequence differs from the sequence ACGGCAATTTTGTGGAT (SEQ ID NO:10) by not more than 5 deletions, insertions and/or substitutions.

16. An expression vector according to claim 15 wherein the intervening sequence differs from the sequence ACGGCAATTTTGTGGAT (SEQ ID NO:10) by not more than 2 deletions, insertions and/or substitutions.

17. An expression vector according to claim, 10 wherein the promoter (i) has the following base sequence:

TTGTAAACGGCAATTTTGTGGATTAAGGT (SEQ ID NO:5).

18. An expression vector for expressing in *E. coli* a polypeptide other than *E. coli* malate dehydrogenase coded for by a DNA coding sequence, said vector comprising (1) an *E. coli* mdh gene promoter having the sequence,

TTGTAAACGGCAATTTTGTGGATTAAGGT (SEQ ID NO:5)

and (2) a restriction enzyme site arranged in relation to said promoter so as to allow introduction of the DNA coding sequence into the vector whereby said coding sequence is operatively linked to the promoter, and wherein if the initiation codon of the DNA sequence is not ATG it is changed to ATG.

19. An expression vector according to claim 17 further comprising the DNA coding sequence which has been introduced into the vector an operatively linked to the promoter and in which the promoter is capable of controlling expression of the polypeptide.

20. A recombinant DNA molecule comprising a DNA coding sequence and including an initiation codon operatively linked to an upstream sequence located upstream of the initiation codon, characterised in that the DNA coding sequence codes for a polypeptide other than *E. coli* malate dehydrogenase and said upstream sequence consists of the 285 base pair sequence GCA TGC AAA TTC TGC TTA AAA GTA AAT TAA
TTG TTA TCA AAT TGA TGT TGT TTT GGC TGA
ACG GTA GGG TAT ATT GTC ACC ACC TGT TGG
AAT GTT GCG CTA ATG CAT AAG CGA CTG TTA
ATT ACG TAA GTT AGG TTC CTG ATT ACG GCA
ATT AAA TGC ATA AAC GCT AAA CTT GCG TGA
CTA CAC ATT CTT GAG ATG TGG TCA TTG TAA
ACG GCA ATT TTG TGG ATT AAG GTC GCG GCA
GCG GAG CAA CAT ATC TTA GTT TAT CAA TAT
AAT AAG GAG TTT CAT (SEQ ID NO:3), and wherein if the initiation codon of the DNA sequence is not ATG it is changed to ATG.

21. A process for producing a polypeptide by expressing a DNA coding sequence, which process comprises culturing a transformed microorganism of the species *E. coli* wherein (i) said transformed microorganism includes a plasmid comprising said DNA sequence, (ii) the initiation codon of said DNA sequence is changed to ATG, (iii) said DNA sequence is operatively linked to a promoter which is an *E. coli* mdh promoter and (iv) said polypeptide is expressed such that it forms between 15 and 60% of the soluble cell protein.

22. A process according to claim 21 wherein said polypeptide forms between 40 and 55% of the soluble cell protein.

23. A process according to claim 21 wherein said polypeptide forms about 50% of the soluble cell protein.

24. A process according to claim 21 wherein said promoter is composed of from between 12 to 50 bases.

25. A process according to claim 24 wherein said promoter is composed of from between 20 to 35 bases.

26. A process according to claim 25 wherein said promoter is composed of about 29 bases.

27. A process according to claim 26 wherein said promoter has a 5' end and a 3 ' end and wherein said promoter comprises the sequence TTGACA (SEQ ID NO:1) at the 5' end and the sequence TTAACT (SEQ ID NO:11) at the 3 ' end.

28. A process according to claim 24 wherein said DNA coding sequence is operatively linked to a ribosome binding site comprising one of the following sequences:

(1) T A A G G A G T T T C A T A T G (SEQ ID NO:16)

(2) A C A G G A A A C A C A T A T G (SEQ ID NO:17).

29. A process according to claim 24 wherein the DNA coding sequence has the initiation codon ATG.

30. A process for producing protein L by expressing DNA sequence coding for protein L which process comprises culturing a transformed microorganism of the species *E. coli*, wherein (i) said transformed microorganism includes a plasmid comprising said DNA sequence, (ii) if the initiation codon of said DNA sequence is not ATG then it is changed to ATG, (iii) said DNA sequence is operatively linked to a promoter which is an *E. coli* mdh promoter and (iv) said protein L is expressed such that it forms about 15% of the soluble cell protein.

31. A process for producing protein G by expressing a DNA sequence coding for protein G which process comprises culturing a transformed microorganism of the species *E. coli* wherein (i) said transformed microorganism includes a plasmid comprising said DNA sequence, (ii) if the initiation codon of said DNA sequence is not ATG then it is changed to ATG, (iii) said DNA sequence is operatively linked to a promoter which is an *E. coli* mdh promoter and (iv) said protein G is expressed such that it forms about 25% of the soluble cell protein.

* * * * *

SEQUENCE LISTING ( 1 ) GENERAL INFORMATION:

( i i i ) NUMBER OF SEQUENCES: 25

( 2 ) INFORMATION FOR SEQ ID NO: 1:

( i ) SEQUENCE CHARACTERISTICS:
        ( A ) LENGTH: 6 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO: 1:

```
TTGACA                                                                          6
```

( 2 ) INFORMATION FOR SEQ ID NO: 2:

( i ) SEQUENCE CHARACTERISTICS:
        ( A ) LENGTH: 6 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO: 2:

```
TATAAT                                                                          6
```

( 2 ) INFORMATION FOR SEQ ID NO: 3:

( i ) SEQUENCE CHARACTERISTICS:
        ( A ) LENGTH: 285 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO: 3:

```
GCATGCAAAT TCTGCTTAAA AGTAAATTAA TTGTTATCAA ATTGATGTTG TTTTGGCTGA            60
ACGGTAGGGT ATATTGTCAC CACCTGTTGG AATGTTGCGC TAATGCATAA GCGACTGTTA           120
ATTACGTAAG TTAGGTTCCT GATTACGGCA ATTAAATGCA TAAACGCTAA ACTTGCGTGA           180
CTACACATTC TTGAGATGTG GTCATTGTAA ACGGCAATTT TGTGGATTAA GGTCGCGGCA           240
GCGGAGCAAC ATATCTTAGT TTATCAATAT AATAAGGAGT TTCAT                           285
```

( 2 ) INFORMATION FOR SEQ ID NO: 4:

( i ) SEQUENCE CHARACTERISTICS:
        ( A ) LENGTH: 6 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO: 4:

```
CATATG                                                                          6
```

( 2 ) INFORMATION FOR SEQ ID NO: 5:

( i ) SEQUENCE CHARACTERISTICS:
        ( A ) LENGTH: 29 base pairs (B) TYPE: nucleic acid
(C) STRANDEDNESS: double
(D) TOPOLOGY: linear (ii) MOLECULE TYPE: DNA (genomic)

(xi) SEQUENCE DESCRIPTION: SEQ ID NO: 5:

TTGTAAACGG CAATTTGTG GATTAAGGT                29

(2) INFORMATION FOR SEQ ID NO: 6:

(i) SEQUENCE CHARACTERISTICS:
    (A) LENGTH: 6 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO: 6:

TTGTAA                                         6

(2) INFORMATION FOR SEQ ID NO: 7:

(i) SEQUENCE CHARACTERISTICS:
    (A) LENGTH: 6 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO: 7:

TAAGGT                                         6

(2) INFORMATION FOR SEQ ID NO: 8:

(i) SEQUENCE CHARACTERISTICS:
    (A) LENGTH: 6 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO: 8:

TGGAAT                                         6

(2) INFORMATION FOR SEQ ID NO: 9:

(i) SEQUENCE CHARACTERISTICS:
    (A) LENGTH: 6 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO: 9:

AATGTT                                         6

(2) INFORMATION FOR SEQ ID NO: 10:

(i) SEQUENCE CHARACTERISTICS:
    (A) LENGTH: 17 base pairs
    (B) TYPE: nucleic acid
    (C) STRANDEDNESS: double
    (D) TOPOLOGY: linear (ii) MOLECULE TYPE: DNA (genomic)

( x i ) SEQUENCE DESCRIPTION: SEQ ID NO: 10:

ACGGCAATTT TGTGGAT                                                                          17

( 2 ) INFORMATION FOR SEQ ID NO: 11:

( i ) SEQUENCE CHARACTERISTICS:
        ( A ) LENGTH: 6 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO: 11:

TTAACT                                                                                       6

( 2 ) INFORMATION FOR SEQ ID NO: 12:

( i ) SEQUENCE CHARACTERISTICS:
        ( A ) LENGTH: 6 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO: 12:

TCAATT                                                                                       6

( 2 ) INFORMATION FOR SEQ ID NO: 13:

( i ) SEQUENCE CHARACTERISTICS:
        ( A ) LENGTH: 6 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO: 13:

ACAGTT                                                                                       6

( 2 ) INFORMATION FOR SEQ ID NO: 14:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO: 14:

TAAGGAGGTG                                                                                  10

( 2 ) INFORMATION FOR SEQ ID NO: 15:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO: 15:

AAAGGAGGTG CATATG                                                                           16

( 2 ) INFORMATION FOR SEQ ID NO: 16:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO: 16:

TAAGGAGTTT CATATG                               16

( 2 ) INFORMATION FOR SEQ ID NO: 17:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO: 17:

ACAGGAAACA CATATG                               16

( 2 ) INFORMATION FOR SEQ ID NO: 18:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO: 18:

AGGAGGTGGC ATATGAAGGC AC                        22

( 2 ) INFORMATION FOR SEQ ID NO: 19:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear     ( i i ) MOLECULE TYPE: DNA (genomic)

( x i ) SEQUENCE DESCRIPTION: SEQ ID NO: 19:

GGAGGTGGCA TATGAAGGCA C                         21

( 2 ) INFORMATION FOR SEQ ID NO: 20:

( i ) SEQUENCE CHARACTERISTICS:
        ( A ) LENGTH: 45 base pairs
        ( B ) TYPE: nucleic acid
        ( C ) STRANDEDNESS: double
        ( D ) TOPOLOGY: linear     ( i i ) MOLECULE TYPE: DNA (genomic)

( i x ) FEATURE:
        ( A ) NAME/KEY: CDS
        ( B ) LOCATION: 31..45

( x i ) SEQUENCE DESCRIPTION: SEQ ID NO: 20:

GAAGGCCCTG GGCTAAAAAG GAGGTGGACG GTG AAG GCA CCC GTA          45
                                  Met Lys Ala Pro Val
                                   1               5

( 2 ) INFORMATION FOR SEQ ID NO: 21:

( i ) SEQUENCE CHARACTERISTICS:
        ( A ) LENGTH: 5 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 21:

```
Met  Lys  Ala  Pro  Val
 1                    5
```

( 2 ) INFORMATION FOR SEQ ID NO: 22:

( i ) SEQUENCE CHARACTERISTICS:
        ( A ) LENGTH: 45 base pairs
        ( B ) TYPE: nucleic acid
        ( C ) STRANDEDNESS: double
        ( D ) TOPOLOGY: linear     ( i i ) MOLECULE TYPE: DNA (genomic)

( i x ) FEATURE:
        ( A ) NAME/KEY: CDS
        ( B ) LOCATION: 31..45

( x i ) SEQUENCE DESCRIPTION: SEQ ID NO: 22:

```
GAAGGCCCTG GGCTAAAAAG GAGGTAACAT ATG AAG GCA CCC GTA           45
                                Met Lys Ala Pro Val
                                 1                5
```

( 2 ) INFORMATION FOR SEQ ID NO: 23:

( i ) SEQUENCE CHARACTERISTICS:
        ( A ) LENGTH: 5 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 23:

```
Met  Lys  Ala  Pro  Val
 1                    5
```

( 2 ) INFORMATION FOR SEQ ID NO: 24:

( i ) SEQUENCE CHARACTERISTICS:
        ( A ) LENGTH: 1598 base pairs
        ( B ) TYPE: nucleic acid
        ( C ) STRANDEDNESS: double
        ( D ) TOPOLOGY: linear     ( i i ) MOLECULE TYPE: DNA (genomic)

( i x ) FEATURE:
        ( A ) NAME/KEY: CDS
        ( B ) LOCATION: 286..1269

( i x ) FEATURE:
        ( A ) NAME/KEY: -10_signal
        ( B ) LOCATION: 228..233

( i x ) FEATURE:
        ( A ) NAME/KEY: -35_signal
        ( B ) LOCATION: 205..210

( x i ) SEQUENCE DESCRIPTION: SEQ ID NO: 24:

```
GCATGCAAAT TCTGCTTAAA AGTAAATTAA TTGTTATCAA ATTGATGTTG TTTTGGCTGA    60

ACGGTAGGGT ATATTGTCAC CACCTGTTGG AATGTTGCGC TAATGCATAA GCGACTGTTA   120
```

-continued

```
ATTACGTAAG TTAGGTTCCT GATTACGGCA ATTAAATGCA TAAACGCTAA ACTTGCGTGA    180

CTACACATTC TTGAGATGTG GTCATTGTAA ACGGCAATTT TGTGGATTAA GGTCGCGGCA    240

GCGGAGCAAC ATATCTTAGT TTATCAATAT AATAAGGAGT TTCAT ATG AAG GCA        294
                                                    Met Lys Ala
                                                     1
```

| | | | | | | | | | | | | | | | | |
|---|---|---|---|---|---|---|---|---|---|---|---|---|---|---|---|---|
| CCC | GTA | CGC | GTG | GCG | GTT | ACC | GGA | GCC | GCG | GGA | CAG | ATC | GGC | TAC | AGC | 342 |
| Pro | Val | Arg | Val | Ala | Val | Thr | Gly | Ala | Ala | Gly | Gln | Ile | Gly | Tyr | Ser | |
| | 5 | | | | 10 | | | | | 15 | | | | | | |
| CTC | CTC | TTC | CGC | ATC | GCC | GCG | GGG | GAG | ATG | CTG | GGC | AAG | GAC | CAG | CCG | 390 |
| Leu | Leu | Phe | Arg | Ile | Ala | Ala | Gly | Glu | Met | Leu | Gly | Lys | Asp | Gln | Pro | |
| 20 | | | | | 25 | | | | | 30 | | | | | 35 | |
| GTG | ATC | CTC | CAG | CTT | TTG | GAG | ATC | CCC | CAG | GCC | ATG | AAG | GCC | CTG | GAG | 438 |
| Val | Ile | Leu | Gln | Leu | Leu | Glu | Ile | Pro | Gln | Ala | Met | Lys | Ala | Leu | Glu | |
| | | | | 40 | | | | | 45 | | | | | 50 | | |
| GGC | GTG | GTC | ATG | GAG | CTG | GAG | GAC | TGC | GCC | TTC | CCC | CTG | CTT | GCG | GGC | 486 |
| Gly | Val | Val | Met | Glu | Leu | Glu | Asp | Cys | Ala | Phe | Pro | Leu | Leu | Ala | Gly | |
| | | | 55 | | | | | 60 | | | | | 65 | | | |
| CTC | GAG | GCC | ACC | GAC | GAC | CCC | AAG | GTG | GCC | TTC | AAG | GAC | GCC | GAC | TAC | 534 |
| Leu | Glu | Ala | Thr | Asp | Asp | Pro | Lys | Val | Ala | Phe | Lys | Asp | Ala | Asp | Tyr | |
| | | 70 | | | | | 75 | | | | | 80 | | | | |
| GCC | CTC | CTG | GTG | GGG | GCG | GCC | CCC | CGC | AAG | GCG | GGG | ATG | GAG | CGC | CGG | 582 |
| Ala | Leu | Leu | Val | Gly | Ala | Ala | Pro | Arg | Lys | Ala | Gly | Met | Glu | Arg | Arg | |
| | 85 | | | | | 90 | | | | | 95 | | | | | |
| GAC | CTT | TTG | CAG | GTA | AAC | GGC | AAG | ATC | TTC | ACC | GAG | CAG | GGC | CGG | GCC | 630 |
| Asp | Leu | Leu | Gln | Val | Asn | Gly | Lys | Ile | Phe | Thr | Glu | Gln | Gly | Arg | Ala | |
| 100 | | | | | 105 | | | | | 110 | | | | | 115 | |
| CTG | GCC | GAG | GTG | GCC | AAG | AAG | GAC | GTC | AAG | GTG | CTG | GTG | GTG | GGC | AAC | 678 |
| Leu | Ala | Glu | Val | Ala | Lys | Lys | Asp | Val | Lys | Val | Leu | Val | Val | Gly | Asn | |
| | | | | 120 | | | | | 125 | | | | | 130 | | |
| CCC | GCC | AAC | ACC | AAC | GCC | CTC | ATC | GCC | TAC | AAG | AAC | GCC | CCC | GGC | CTC | 726 |
| Pro | Ala | Asn | Thr | Asn | Ala | Leu | Ile | Ala | Tyr | Lys | Asn | Ala | Pro | Gly | Leu | |
| | | | 135 | | | | | 140 | | | | | 145 | | | |
| AAC | CCC | CGG | AAC | TTC | ACC | GCC | ATG | ACC | CGG | CTG | GAC | CAC | AAC | CGG | GCC | 774 |
| Asn | Pro | Arg | Asn | Phe | Thr | Ala | Met | Thr | Arg | Leu | Asp | His | Asn | Arg | Ala | |
| | | 150 | | | | | 155 | | | | | 160 | | | | |
| AAG | GCC | CAG | CTC | GCC | AAG | AAG | ACC | GGG | ACG | GGC | GTG | GAC | CGC | ATC | CGC | 822 |
| Lys | Ala | Gln | Leu | Ala | Lys | Lys | Thr | Gly | Thr | Gly | Val | Asp | Arg | Ile | Arg | |
| 165 | | | | | 170 | | | | | 175 | | | | | | |
| CGC | ATG | ACG | GTG | TGG | GGC | AAC | CAC | TCC | TCC | ACC | ATG | TTC | CCC | GAC | CTC | 870 |
| Arg | Met | Thr | Val | Trp | Gly | Asn | His | Ser | Ser | Thr | Met | Phe | Pro | Asp | Leu | |
| 180 | | | | | 185 | | | | | 190 | | | | | 195 | |
| TTC | CAC | GCC | GAG | GTG | GAC | GGC | AGG | CCC | GCC | CTG | GAG | CTC | GTG | GAC | ATG | 918 |
| Phe | His | Ala | Glu | Val | Asp | Gly | Arg | Pro | Ala | Leu | Glu | Leu | Val | Asp | Met | |
| | | | | 200 | | | | | 205 | | | | | 210 | | |
| GAG | TGG | TAC | GAG | AAG | GTC | TTC | ATC | CCC | ACC | GTG | GCC | CAG | CGG | GGG | GCG | 966 |
| Glu | Trp | Tyr | Glu | Lys | Val | Phe | Ile | Pro | Thr | Val | Ala | Gln | Arg | Gly | Ala | |
| | | | 215 | | | | | 220 | | | | | 225 | | | |
| GCC | ATC | ATC | CAG | GCC | CGG | GGG | GCC | AGC | AGC | GCC | GCC | AGC | GCC | GCG | AAC | 1014 |
| Ala | Ile | Ile | Gln | Ala | Arg | Gly | Ala | Ser | Ser | Ala | Ala | Ser | Ala | Ala | Asn | |
| | | 230 | | | | | 235 | | | | | 240 | | | | |
| GCC | GCC | ATA | GAG | CAC | ATC | CGC | GAC | TGG | GCC | CTG | GGC | ACC | CCG | GAG | GGG | 1062 |
| Ala | Ala | Ile | Glu | His | Ile | Arg | Asp | Trp | Ala | Leu | Gly | Thr | Pro | Glu | Gly | |
| | 245 | | | | | 250 | | | | | 255 | | | | | |
| GAC | TGG | GTT | TCC | ATG | GCC | GTC | CCC | TCC | CAA | GGG | GAG | TAC | GGC | ATC | CCC | 1110 |
| Asp | Trp | Val | Ser | Met | Ala | Val | Pro | Ser | Gln | Gly | Glu | Tyr | Gly | Ile | Pro | |
| 260 | | | | | 265 | | | | | 270 | | | | | 275 | |
| GAG | GGC | ATC | GTC | TAC | TCC | TTC | CCG | GTG | ACG | GCC | AAG | GAC | GGG | GCG | TAC | 1158 |
| Glu | Gly | Ile | Val | Tyr | Ser | Phe | Pro | Val | Thr | Ala | Lys | Asp | Gly | Ala | Tyr | |
| | | | | 280 | | | | | 285 | | | | | 290 | | |

```
CGG GTC GTG GAG GGC CTG GAG ATC AAC GAG TTC GCC CGC AAG CGC ATG      1206
Arg Val Val Glu Gly Leu Glu Ile Asn Glu Phe Ala Arg Lys Arg Met
            295                 300                 305

GAG ATC ACG GCC CAG GAA CTT CTG GAC GAG ATG GAG CAG GTG AAG GCC      1254
Glu Ile Thr Ala Gln Glu Leu Leu Asp Glu Met Glu Gln Val Lys Ala
        310                 315                 320

CTG GGC CTC ATC TGAGAGGCTG GCCTCAGAGC CCCCACCGCG CCCTGCGGTG          1306
Leu Gly Leu Ile
        325

GGGGCTTTAC ACCACCCCAT GCTGGCTTGC GCCAGCATGG GGCCCCGGC AAAAGCTCCC     1366

TGGGGAGCTT CCCCGGGCCC GTCGGGCGAA GGCAACCGGA AGGGTATTAG CCTTTGGGCC    1426

AGGCCTCGAG GGCCCAAGGG TAGACCACCC AGGCCGCCGT CTCCTCGGCG TAGAAGTCGG    1486

GGCGGTCCGG CACCCGGTTC CGCCCCGGCT TGAAGTGGAG GGTGGCCACC ACAGGCACCC    1546

CGCCCGCCCG GCGCACCCGG GCCTTCACGG CAAAGGCCGT GCGCCCCGAG TC            1598
```

( 2 ) INFORMATION FOR SEQ ID NO: 25:

( i ) SEQUENCE CHARACTERISTICS:
        ( A ) LENGTH: 327 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO: 25:

```
Met Lys Ala Pro Val Arg Val Ala Val Thr Gly Ala Ala Gly Gln Ile
 1               5                  10                  15

Gly Tyr Ser Leu Leu Phe Arg Ile Ala Ala Gly Glu Met Leu Gly Lys
            20                  25                  30

Asp Gln Pro Val Ile Leu Gln Leu Leu Glu Ile Pro Gln Ala Met Lys
        35                  40                  45

Ala Leu Glu Gly Val Val Met Glu Leu Glu Asp Cys Ala Phe Pro Leu
    50                  55                  60

Leu Ala Gly Leu Glu Ala Thr Asp Asp Pro Lys Val Ala Phe Lys Asp
65                  70                  75                  80

Ala Asp Tyr Ala Leu Leu Val Gly Ala Ala Pro Arg Lys Ala Gly Met
                85                  90                  95

Glu Arg Arg Asp Leu Leu Gln Val Asn Gly Lys Ile Phe Thr Glu Gln
            100                 105                 110

Gly Arg Ala Leu Ala Glu Val Ala Lys Lys Asp Val Lys Val Leu Val
        115                 120                 125

Val Gly Asn Pro Ala Asn Thr Asn Ala Leu Ile Ala Tyr Lys Asn Ala
    130                 135                 140

Pro Gly Leu Asn Pro Arg Asn Phe Thr Ala Met Thr Arg Leu Asp His
145                 150                 155                 160

Asn Arg Ala Lys Ala Gln Leu Ala Lys Lys Thr Gly Thr Gly Val Asp
                165                 170                 175

Arg Ile Arg Arg Met Thr Val Trp Gly Asn His Ser Ser Thr Met Phe
            180                 185                 190

Pro Asp Leu Phe His Ala Glu Val Asp Gly Arg Pro Ala Leu Glu Leu
        195                 200                 205

Val Asp Met Glu Trp Tyr Glu Lys Val Phe Ile Pro Thr Val Ala Gln
    210                 215                 220

Arg Gly Ala Ala Ile Ile Gln Ala Arg Gly Ala Ser Ser Ala Ala Ser
225                 230                 235                 240
```

-continued

| Ala | Ala | Asn | Ala | Ala | Ile | Glu | His | Ile | Arg | Asp | Trp | Ala | Leu | Gly | Thr |
|---|---|---|---|---|---|---|---|---|---|---|---|---|---|---|---|
| | | | | 245 | | | | | 250 | | | | | 255 | |
| Pro | Glu | Gly | Asp | Trp | Val | Ser | Met | Ala | Val | Pro | Ser | Gln | Gly | Glu | Tyr |
| | | | 260 | | | | | 265 | | | | | 270 | | |
| Gly | Ile | Pro | Glu | Gly | Ile | Val | Tyr | Ser | Phe | Pro | Val | Thr | Ala | Lys | Asp |
| | | 275 | | | | | 280 | | | | | 285 | | | |
| Gly | Ala | Tyr | Arg | Val | Val | Glu | Gly | Leu | Glu | Ile | Asn | Glu | Phe | Ala | Arg |
| | 290 | | | | | 295 | | | | | 300 | | | | |
| Lys | Arg | Met | Glu | Ile | Thr | Ala | Gln | Glu | Leu | Leu | Asp | Glu | Met | Glu | Gln |
| 305 | | | | | 310 | | | | | 315 | | | | | 320 |
| Val | Lys | Ala | Leu | Gly | Leu | Ile | | | | | | | | | |
| | | | | 325 | | | | | | | | | | | |